United States Patent
Carlopio

(10) Patent No.: US 7,020,899 B1
(45) Date of Patent: Apr. 4, 2006

(54) FLUID IMPERVIOUS CAST PROTECTOR

(76) Inventor: Frank Vincent Carlopio, 911 N. Cordova St., Burbank, CA (US) 91505

( * ) Notice: Subject to any disclaimer, the term of this patent is extended or adjusted under 35 U.S.C. 154(b) by 48 days.

(21) Appl. No.: 10/278,526

(22) Filed: Oct. 23, 2002

(51) Int. Cl.
*A41D 13/08* (2006.01)

(52) U.S. Cl. .................. 2/167; 2/161.1; 2/16; 602/3

(58) Field of Classification Search ............ 2/16, 2/21, 22, 158, 159, 161.1, 161.5, 161.6, 161.7, 2/162, 166, 167, 168, 169, 170, 161.8, 163; 602/3, 20, 21, 23, 62–65; 128/846, 849, 128/856; 441/56, 57, 59–61
See application file for complete search history.

(56) References Cited

U.S. PATENT DOCUMENTS

| | | | |
|---|---|---|---|
| 338,790 A | 3/1886 | Slack | |
| 1,280,421 A | 10/1918 | Diem | |
| 1,762,865 A | 6/1930 | Heinrich | |
| 2,244,871 A | 6/1941 | Guinzburg | |
| 2,683,263 A * | 7/1954 | Lenhart | 2/168 |
| 3,025,403 A * | 3/1962 | Belknap et al. | 250/516.1 |
| 3,391,406 A * | 7/1968 | Lucas | 2/161.6 |
| 3,657,741 A | 4/1972 | Blanco | |
| 4,036,220 A | 7/1977 | Bellasalma | |
| 4,098,268 A * | 7/1978 | Scott | 602/3 |
| 4,139,003 A * | 2/1979 | Little et al. | 602/3 |
| 4,346,699 A * | 8/1982 | Little et al. | 602/3 |
| 4,363,317 A * | 12/1982 | Broucek | 602/3 |
| 4,423,722 A * | 1/1984 | Dickman | 128/880 |
| 4,639,945 A * | 2/1987 | Betz | 2/22 |
| 4,986,265 A | 1/1991 | Caponi | |
| 5,063,919 A * | 11/1991 | Silverberg | 602/3 |
| 5,143,762 A * | 9/1992 | Ho | 428/35.7 |
| 5,452,478 A | 9/1995 | Rombach et al. | |
| 5,575,014 A * | 11/1996 | Kane et al. | 2/239 |
| 5,704,670 A | 1/1998 | Surplus | |
| 5,734,992 A | 4/1998 | Ross | |
| 5,761,746 A * | 6/1998 | Brown | 2/243.1 |
| 5,924,130 A * | 7/1999 | Fragomeli | 2/16 |
| 6,126,621 A * | 10/2000 | Aceves | 602/3 |
| 6,405,381 B1 | 6/2002 | Bowman, Jr. | |
| 6,421,830 B1 | 7/2002 | Reynolds | |
| D479,384 S * | 9/2003 | Sims | D2/617 |
| 2003/0191419 A1* | 10/2003 | Melin et al. | 602/3 |
| 2004/0092852 A1* | 5/2004 | Kruss | 602/21 |

* cited by examiner

*Primary Examiner*—A. Vanatta
(74) *Attorney, Agent, or Firm*—Michael I. Kroll

(57) ABSTRACT

A fluid impervious protective sleeve is described adapted for covering and sealing an injury positioned on a limb of a wearer. The protective sleeve has an elastomeric upper portion sealingly connected with a polymer lower portion. The upper portion defines a waterproof sealing interface adapted for use with a portion of the limb. The sealing interface is configured for accommodating the limb's full range of motion while the wearer is engaged in activities such as water sports. The lower portion 5 cis adapted for use with a wearer's hand or foot.

1 Claim, 6 Drawing Sheets

FLUID IMPERVIOUS CAST PROTECTOR

BACKGROUND OF THE INVENTION

1. Field of the Invention

The present invention relates generally to covers and, more specifically, to fluid impervious protective covers.

2. Description of the Prior Art

Waterproof covers configured for the protection of the arm and leg range from those to assist trappers to protective sleeves for injured limbs. Technological innovations have included linings of various types, waterproof but air permeable materials, and various mechanisms for providing a sealing interface with the wearer.

U.S. Pat. No. 1,280,421

Inventor: Hans J. Diem

Issued: Oct. 1, 1918

This invention is a waterproof, two piece, simply constructed, loosely fitting mitten for covering the hand and arm. The mitten is configured for ease of removal and replacement. A first pie ce of the mitten is a waterproof outer cover constructed of double texture rubberized cloth. The outer cover is configured to fit over a second piece, an inner liner of flannel. Elastic bands are positioned at the arm of the wearer and the wrist. Diem, however, is limited by an elastic band on the upper arm that holds the gauntlet securely, but is not configured as a water-tight seal.

U.S. Pat. No. 1,762,865

Inventor: Paul G. Heinrich

Issued: Jun. 10, 1930

A trapper's waterproof glove is described having a tubular sleeve and hand portion formed of rubber. The tubular sleeve includes a lining adhered to an inside of the tubular sleeve. Elastic bands are positioned closed to the upper end and above the wearer's elbow. Heinrich is limited in the depth of its immersion, however, because the elastic bands are configured for holding the glove in position, but not sealing the upper end of the glove against fluids.

U.S. Pat. No. 2,244,871

Inventor: George K. Guinzburg

Issued: Jun. 10, 1941

A waterproof protective device for enclosing limbs including a tubular member configured to enclose a limb having a bandage or a cast to form a watertight seal. The tubular member has two opposing open ends and is configured to provide a waterproof seal about a portion of a limb using one or more elastic inner flanges to preclude fluid from entering the open end. Guinzburg, however, depends upon the positioning of the seal and the combined bias of the tubular member and inner flange to seal the open ends. This kind of sealing mechanism is vulnerable to loosening with perspiration from exercise, is vulnerable to pressure from an external fluid, and concentrates the sealing force on a relatively narrow area which would have a tendency to restrict the blood flow. The tubular member is preferably fabricated of latex or sheet rubber.

U.S. Pat. No. 4,036,220

Inventor: Gerald John Bellasalma

Issued: Jul. 19, 1977

A protective device is described wherein a flexible tubular body member enclosing means has at least one body member securing means. The member securing means includes a foam like cushionable band substantially fixedly positioned upon the exterior surface of one end of the tubular member. The cushionable band includes a cantilevered portion extending from the tubular member that is configured for overlapping the fixedly positioned portion. A hook and loop device is positioned on the cushionable band for securing upon itself and sealing the open end of the tubular member. Bellasalma, however, is limited by its fastening means which retains its seal solely by the tightness of the hook and loop device. In addition, while Bellasalma does address sustaining its waterproof seal while bathing, it does not address how the cushionable band adapts to sustain its sealing interface during exercising when muscles are changing their circumference while immersed in water or in the rain, for example. Further, the added circumferential dimension of the cushionable band can readily result in chafing and increases the chances that it will be loosened during active physical use.

U.S. Pat. No. 4,986,265

Inventor: Ronald E. Caponi

Issued: Jan. 22, 1991

A protective cover for a plaster cast includes an elongated waterproof, flexible, polymer bag having an opening in one end thereof. The open end of the polymer bag has an elastic edge to hold the elongated, waterproof, flexible, polymer bag over a cast on a patient's limb. A small connector of book and loop material is positioned in the vicinity of the opening of the flexible bag. An elongated, substantially flat sealing band is made of an elastic, resilient, waterproof foamed polymer material and has hook and loop material attached thereto. The bag is placed over a cast, the sealing band attached near the open end to the bag, and the sealing band is wrapped around the open end thereof in multiple overlapping wraps to seal the open end against the intrusion of liquid. Caponi, however, is limited by its requirement for the combination of the two independent sealing mechanisms to be functional to form a reliable waterproof seal. In addition, the ability of the sealing band to remain fixedly positioned relative to the open end during exercise or athletic activity when there is repetitive muscle flexing is strongly suspect.

U.S. Pat. No. 5,734,992

Inventor: Michael R. Ross

Issued: Apr. 7, 1998

An extended protective article capable of covering an upper extremity of a wearer from the hand and up to a region near the axilla, and providing protection from fluids from its distal to its proximal ends; the protective article can be formed of a single material or two components of dissimilar materials. Cinching means are positioned at the wrist and at a proximal end of the glove. The cinching means of Ross, however is limited as it does not provide a waterproof sealing interface between the wearer and the glove.

U.S. Pat. No. 6,421,830

Inventor: David V. Reynolds

Issued: Jul. 23, 2002

A method and apparatus for installing a water resistant sleeve on a limb using one hand. Reynolds uses a pliable hem connected to a proximate end of the sleeve and floldable in an accordion fashion when drawn closed to fit sealingly around the portion of the user's body. An elongate elastic flat strip extending through the hem is drawn closed sealing the hem means against the portion of the user's body. An engagement means is used to fix the tension in the flat strip. Reynolds, however, is limited by its total dependence upon the integrity of the grip of the engagement means on the flat strip for the effectiveness of its sealing mechanism. In addition, the flat strip and engagement means extending from the sleeve would chafe and be at risk for loosening during exercise. Further, the engagement means is limited in its ability to expand and contract with the muscle flexing.

A continuing need exists for a fluid impervious cover adapted for use with a limb of a wearer and configured for sustaining its fluid impervious seal on the wearer during physical exercise.

SUMMARY OF THE PRESENT INVENTION

A primary object of the present invention is to provide a fluid impervious protective cover having a waterproof sealing interface with a wearer.

Another object of the present invention is to provide a fluid impervious protective cover for a limb including a thin layered upper portion and lower portion, the upper portion being configured for providing the waterproof sealing interface with the wearer and being compatible with the exercising of the limb in water sports.

Still yet another object of the present invention is to provide a fluid impervious protective cover configured as a limb protector that covers from a distal end of the foot up to as far as the thigh region and thereby protect a cast from water while exercising and/or submerged in water.

Another object of the present invention is to provide a fluid impervious protective cover configured for covering from the distal end of the hand up to a region just above the biceps muscle and just below the deltoid muscle, the cover providing protection from fluids that could enter the cast and create fungus or mildew.

Yet another object of the present invention is to provide a fluid impervious protective cover configured as a glove that includes an upper portion configured for making a sealing interface, the upper portion encompassing the lower region of the biceps muscle to the upper portion of the biceps muscle and just below the deltoid.

Still yet another object of the present invention is to provide a fluid impervious protective cover configured as a glove, the glove including an upper portion configured to accommodate the arm maintaining muscle flexibility throughout a full range of motion while sustaining a sealing interface and preventing fluids from entering the glove.

Another object of the present invention is to provide a fluid impervious protective cover including the lower portion constructed from a polymeric material that is also fluid impervious.

Yet another object of the present invention is to provide a fluid impervious protective cover including the upper portion, the upper portion being configured for accommodating the complete flexure of the muscles of the upper arm, preventing drift of the elastomeric member up or down the arm.

Still yet another object of the present invention is to provide a fluid impervious protective cover that allows the wearer having the cast to submerge their arm in water without fear of seepage of fluids, which can cause mildew and fungus growth within the cast, the present invention being ideal for water sport oriented adults and children as well as those who can wear the device in a shower, tube, or pool.

Additional objects of the present invention will appear as the description proceeds. The invention, together with attendant advantages, will be best understood by reference to the following detailed description of the invention when used in conjunction with the figures below.

DESCRIPTION OF THE REFERENCED NUMERALS

Turning now to the reference numerals used, the following numbering is used throughout the various drawing figures:

10 fluid impervious protective sleeve
30 lower portion of protective sleeve
32 distal end portion of lower portion
34 proximal end portion of lower portion
50 upper portion of protective sleeve
52 distal end of protective sleeve
54 proximal end of protective sleeve
100 arm of a wearer
103 epidermis of the wearer
105 brachial muscle of the wearer
110 triceps of the wearer
120 biceps of the wearer
150 cast
175 leg of the wearer

BRIEF DESCRIPTION OF THE DRAWING FIGURES

Preferred embodiments of the presently disclosed fluid impervious protective cover are described herein with reference to the drawings, wherein.

DETAILED DESCRIPTION OF THE PREFERRED EMBODIMENT

Figure 1:
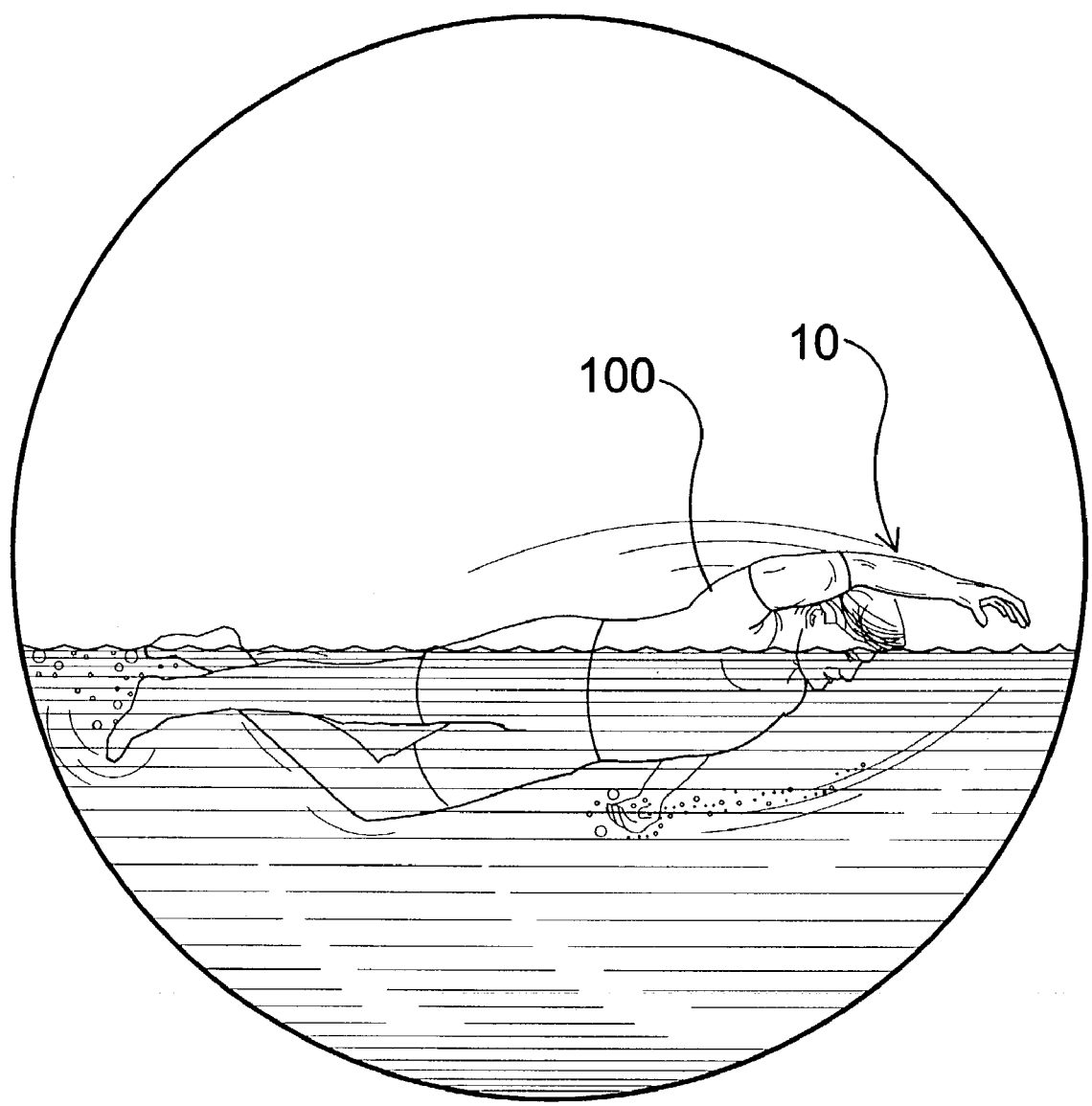
FIG. 1 is a partial cross-sectional view of a fluid impervious protective cover configured as a glove positioned on a limb of a wearer constructed in accordance with the present disclosure.

Referring now in specific detail to the drawings in which like referenced numerals identify similar or identical elements throughout the several views, and initially to FIG. 1, a novel fluid impervious protective limb sleeve or cover 10 is shown adapted for use over at least a portion of a limb of a wearer during athletic activities. Athletic activities as defined herein include swimming in water and exercising in inclement weather such as jogging in the rain. Limb protective cover 10 is configured to cover the wearer's injured area and preclude fluids from entering inside limb cover 10 independent of the position or the limb or the activity the wearer is engaged in while wearing protective cover 10.

Protective cover 10 in this first preferred embodiment is configured to cover the injured area of the wearer and extend proximally from the fingers as far as the upper regions or axilla of the wearer's arm 100. Protective sleeve 10 is a thin layer of material suitable for accommodating the full range of motion of the limb of the wearer without violating the integrity of the seal of fluid impervious protective cover 10. This ensures the injured area is protected from undesirable effects of water intrusion. Undesirable effects of water intrusion as defined herein include, but are not limited to, for example fungus, mildew, viruses, or bacterias from entering inside cover 10.

Figure 2:
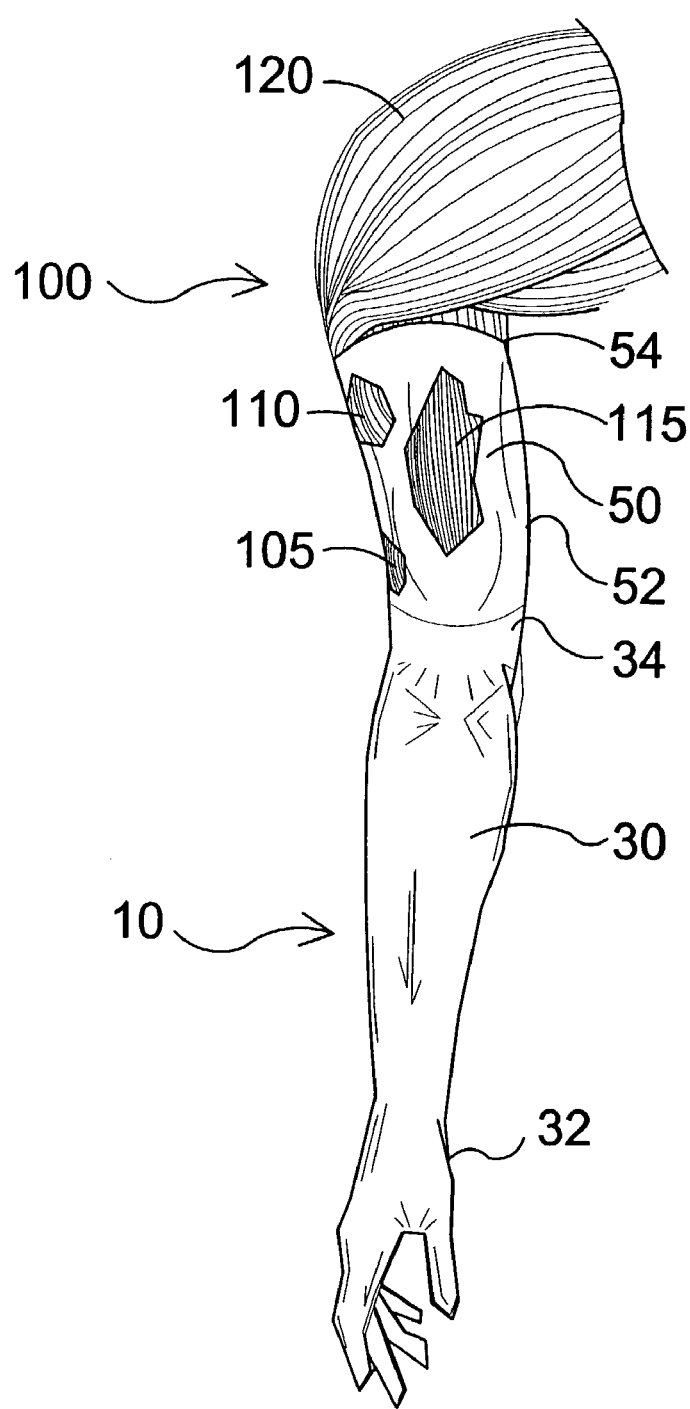
FIG. 2 is an illustrative frontal view of the fluid impervious cover of FIG. 1 positioned on the wearer.

In FIG. 2 protective cover 10 includes a lower portion 30 connected to an upper portion 50. Lower portion 30 has a distal end portion 32 and a proximal end 34. Lower portion 30 has a generally tubular shape with distal end portion 32 being a closed and sealed end and proximal end 34 defining an approximately circular opening. Distal end portion 32, in this one preferred embodiment, defines a generally form fitting glove with fingers adapted for the positioning of a hand of the wearer. Lower portion 30 is fabricated from a polymeric material and is constructed to be fluid impervious. Lower portion 30 can be configured to be loosely fitting without any stretchable material qualities or stretchable such that lower portion 30 has a bias and is generally configured to conform to the shape of the limb positioned therein depending upon the desired use of protective cover 10.

Upper portion 50 has a distal end 52 and a proximal end 54 defining a tubular shaped member. Distal end 52 is connected to proximal end 34. As shown, upper portion 50 is suitable for positioning on the forearm or on the region of the biceps 115 and triceps 110 muscles.

In this first preferred embodiment, upper portion 50 has a length extending from approximately the lower region of brachial muscle 105 and biceps muscle 115 to the upper portion of biceps 115 and just below the deltoid muscle 120 of arm 100. Upper portion 50 is adapted to define a waterproof sealing interface with the limb of the wearer as a result of the combination of its positioning, length, and the bias inherent in the material with which upper portion 50 is fabricated.

The extended length of the sealing interface is aided by upper portion 50 being adapted for positioning around what are normally tapered muscle groups including those associated with brachiaradialis of the forearm, biceps 115 of the upper arm, gastrocremius of the calf, and rectus femoris of the thigh. These muscles generally taper distally and proximally from an approximately centrally positioned muscular peak.

The length of upper portion 50 is also configured to accommodate the repeated flexing of the muscles of the limb of the wearer without losing the integrity of its waterproof seal with the limb of the wearer. The extended length has the further advantage of spreading the biased load of the material over a broader surface area. This lessens the discomfort and reduces the restriction of the blood within the limb of the wearer. In addition, upper portion 50 as a single relatively thin layer of material is configured for supporting a full range of motion of the limb of the wearer while maintaining the integrity of the seal with the wearer's limb.

Upper portion 50 is preferably fabricated of an elastomeric material having sufficient characteristics for stretching and bias such that upper portion 50 securely defines the sealing interface with its position on the limb of the wearer. The stretch of upper portion 50 is configured for being uniformly distributed along the length of upper portion 50 or selectively increased in the vicinity of proximal end 54 and distal end 52.

Proximal end 34 of lower portion 30 and distal end 52 of upper portion 50 are connected to form a waterproof seal using means for joining suitable for their respective materials. Means for joining can include heating, bonding, or fusing the materials and/or the use of adhesives to form a fluid impervious seal between upper portion 50 and lower portion 30.

Protective sleeve 10 is fabricated in a range of sizes configured for mating with the stretch and bias characteristics of the material of upper portion 50 and the circumference of the position on the limb where upper portion 50 will provide its sealing interface. The range of sizes extends from those suitable for infants to large oversized adults. In addition, it is envisioned that the present disclosure can be readily adapted for use as a protective sleeve for animals.

Figure 3:
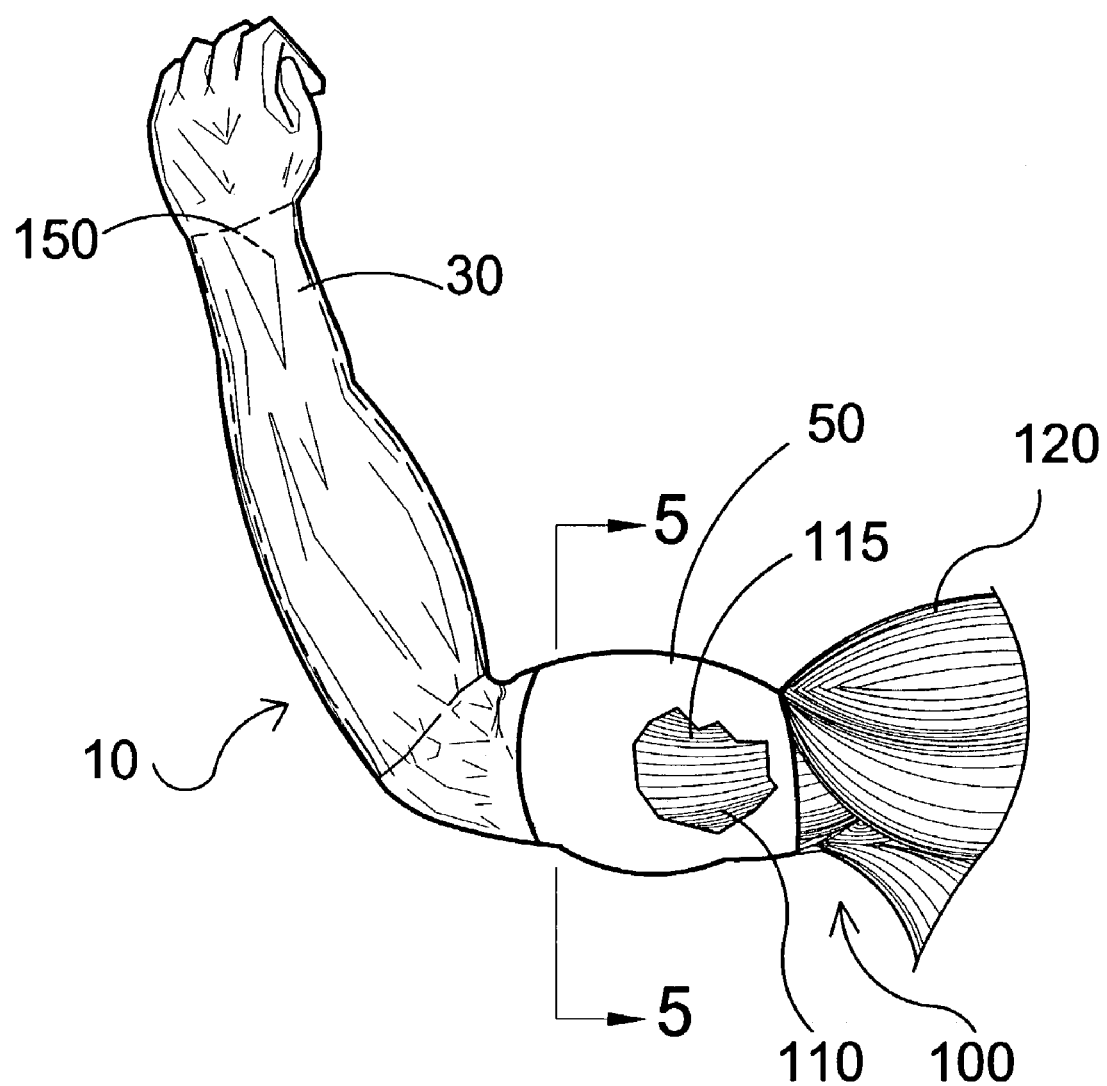
FIG. 3 is an illustrative side view of the fluid impervious cover of FIG. 1 positioned on a slightly bent arm of the wearer.

FIG. 3 shows protective sleeve 10 in use positioned on the flexed arm 100 of the wearer. Upper portion 50 is positioned from the lower region of biceps muscle 115 to the upper portion of biceps muscle 115 and just below deltoid muscle 120. The bias of upper portion 50 fixes upper portion 50 in position on arm 100 even as the wearer's triceps 110 and biceps 115 muscles are flexed. In addition, as upper portion 50 stretches with the flexing of the muscles of arm 100, for example, as a result of the bias of the elastomeric material, a sealing interface with arm 100 is sustained while the circumference of arm 100 changes between a relaxed and flexed position.

Lower portion 30 encompasses a cast 150 or any other form of injured portion of a limb of the wearer. The term cast 150 as used herein is thus representative of any type of injury potentially requiring the use of protective sleeve 10 to include examples such as, but not limited to, injuries requiring bandages, stitches, braces, splints, pins, etc.

The positioning of protective sleeve 10 on arm 100 of the wearer in this one preferred embodiment includes determining a correct size for the wearer, positioning protective sleeve 10 on the wearer from an everted position to an extended position along the predetermined length of the limb. In the first preferred embodiment, lower portion 30 is cooperatively fit with the hand of the wearer and extended up the arm. Upper portion 50 is stretched over and positioned on the biceps 115 and triceps 110 muscles as described previously from the region above the elbow to the axilla to initiate a waterproof sealing interface with the wearer's arm 100. Protective sleeve 10 is removed by simply peeling away sleeve 10, starting with upper portion 50, from the limb of the wearer.

Figure 4:
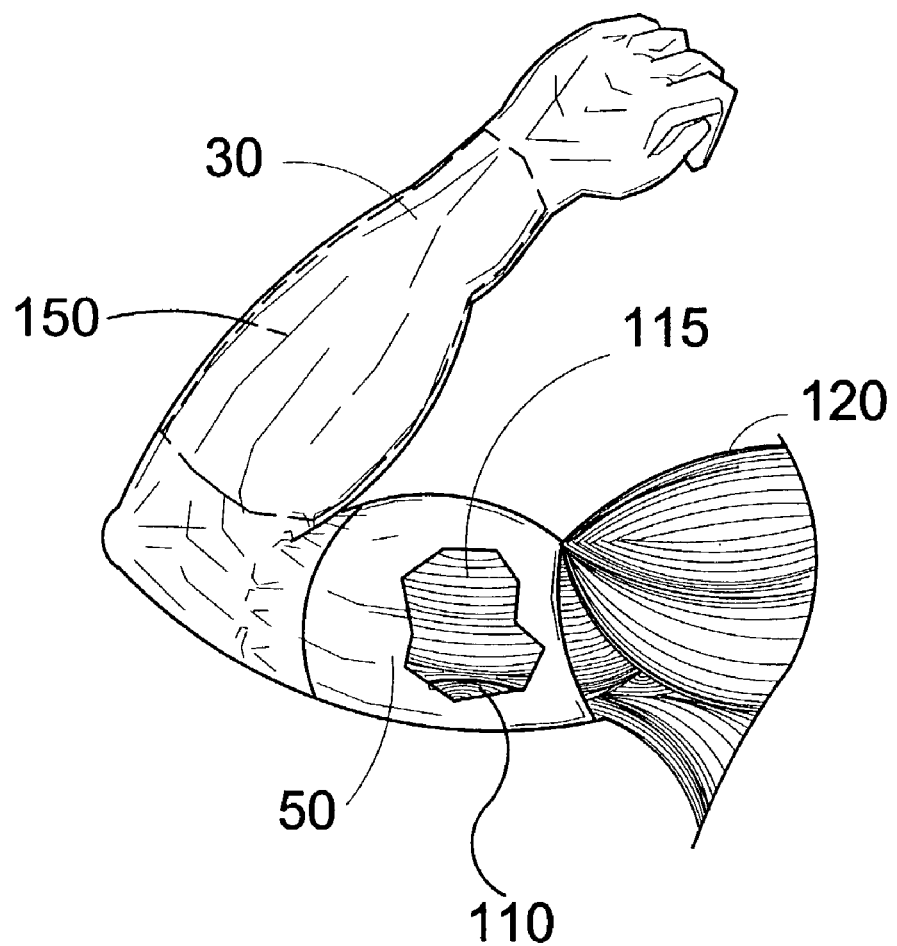
FIG. 4 is an illustrative side view of the fluid impervious cover of FIG. 1 positioned on a fully bent arm of the wearer.

FIG. 4 shows protective sleeve 10 on arm 100 of the wearer with the wearer's upper arm 100 in a fully flexed position. Upper portion 50 stretches, but the bias of the material continues to encompass the length between the lower region of the biceps muscle 115 to the upper portion of the biceps muscle 115 and just below the deltoid 120 and provide a sealing interface with the wearer. Upper portion 50 stretches to accommodate a full range of motion and muscle flexibility of the limb of the wearer while preventing fluids from entering.

Figure 5:
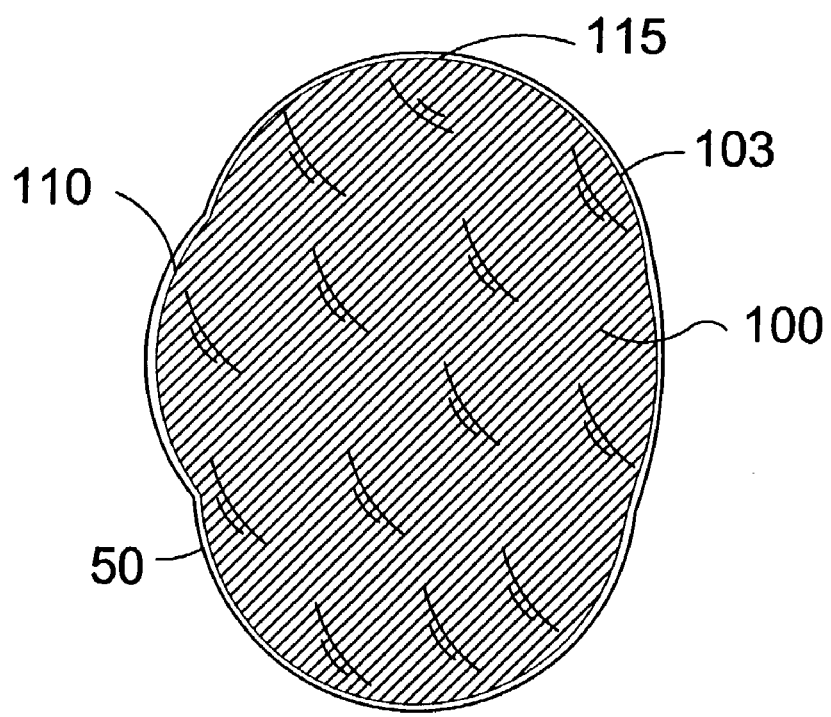
FIG. 5 is a cross sectional view of the fluid impervious cover along line 5—5 of FIG. 3.

FIG. 5 shows a cross sectional view of protective sleeve 10 positioned on arm 100 of the wearer in the region of triceps muscle 110. The conforming bias is apparent from the direct and uninterrupted contact between upper portion 50 and epidermis 103 around the complete circumference of arm 100. Protective sleeve 10 is a thin layer of protective material configured for sustaining a waterproof seal during water sports, for example, by the wearer.

Figure 6:
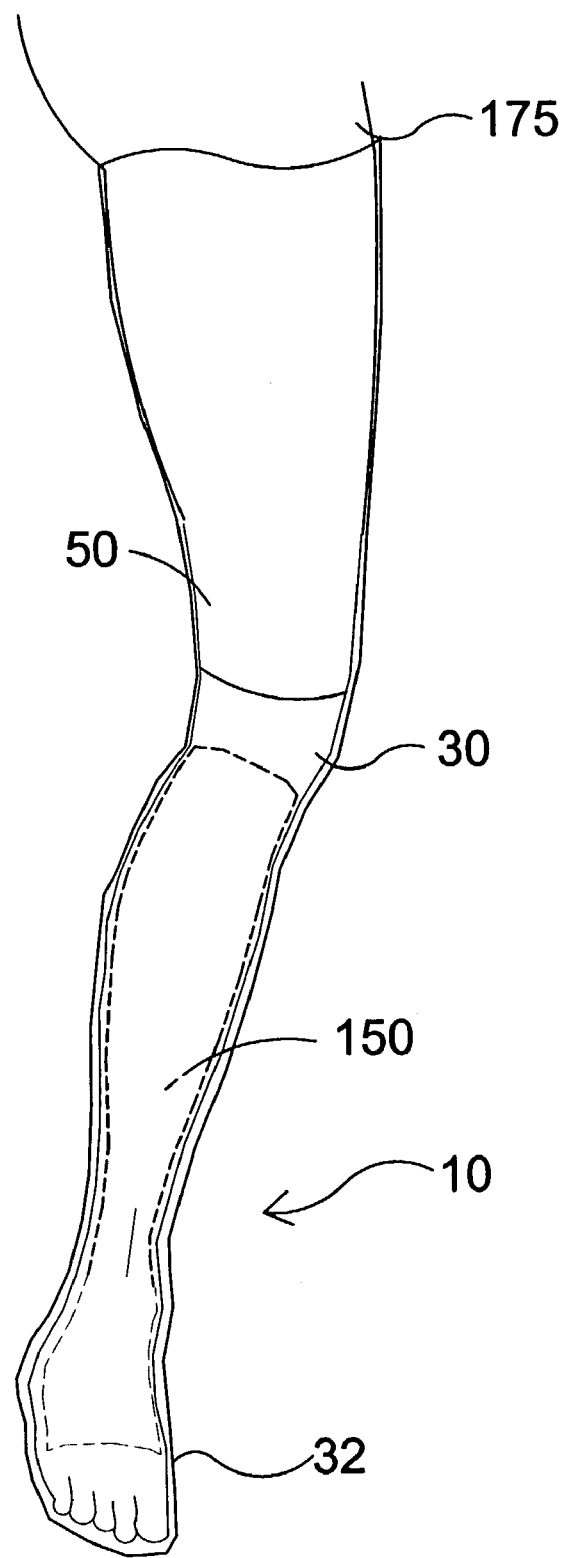
FIG. 6 is an illustrative view of the fluid impervious protective cover configured for positioning on a leg of a wearer constructed in accordance with the present disclosure.

FIG. 6 shows protective sleeve 10 positioned to encompass the wearer's leg 175 from the toes up to as far as the upper thigh region. Upper portion 50 has a length, in this second preferred embodiment, extending from above the knee to the upper regions of the thigh of leg 175. Upper portion 50 has sufficient length to ensure the integrity of the water impervious seal while not inhibiting the range of motion of leg 175. Lower portion 30 covers cast 150 and can include distal end portion 32 having a simple rounded end or multiple appendages for the toes of the wearer.

Protective sleeve 10 is also configurable to extend from the toes up to the calf and the knee region of the wearer. Upper portion 50 in this embodiment is positioned around the wearer's calf.

Although the illustrative embodiments of the present disclosure have been described herein with reference to the accompanying drawings, it is to be understood that the disclosure is not limited to those precise embodiments, and that various other changes and modifications may be affected therein by one skilled in the art without departing from the scope or spirit of the disclosure. All such changes and modifications are intended to be included within the scope of the disclosure.

What is claimed is:

1. A protective fluid impervious sleeve adapted for enclosing at least a portion of an arm a of a wearer consisting of:
    an upper portion having a proximal end and a distal end, the upper portion defining a tubular structure having a finite length and being fabricated of elastomeric material, the upper portion being adapted to define a waterproof sealing interface with an injured portion of the arm of the wearer by providing direct and uninterrupted contact with an underlying surface of skin on said arm and stretchable to accommodate a full range of motion and muscle flexibility of the arm while preventing fluids from entering; and
    a lower portion having a proximal end and a distal end, the proximal end of the lower portion being sealingly connected to the distal end of the upper portion, the distal end of the lower portion defining an end, the lower portion being flexible and loosely fitting to allow exercising of the limb by the wearer, the lower portion being fabricated of a polymer material, the distal end of the lower portion being configured as a glove with separate sleeves for each finger of the wearer.

* * * * *